United States Patent [19]

Hughes

[11] 4,394,866
[45] Jul. 26, 1983

[54] S-A NODE HELICAL LEAD FOR ATRIAL PACEMAKERS AND METHOD OF PLACEMENT

[75] Inventor: Howard C. Hughes, Cornwall, Pa.

[73] Assignee: Research Corporation, New York, N.Y.

[21] Appl. No.: 226,831

[22] Filed: Jan. 21, 1981

[51] Int. Cl.³ ............................................. A61N 1/04
[52] U.S. Cl. .................................. 128/785; 128/786; 128/419 P
[58] Field of Search ............................... 128/784–786, 128/419 P, 642

[56] References Cited

U.S. PATENT DOCUMENTS

| | | | |
|---|---|---|---|
| 3,348,548 | 10/1967 | Chardack | 128/786 |
| 3,596,662 | 8/1971 | Boldus | 128/785 |
| 3,729,008 | 4/1973 | Berkovitz | 128/786 |
| 3,890,977 | 6/1975 | Wilson | 128/786 |
| 3,920,501 | 9/1975 | Citron et al. | 128/785 |
| 3,939,843 | 2/1976 | Smyth | 128/786 |
| 4,026,303 | 5/1977 | Babotai | 128/785 |
| 4,057,067 | 11/1977 | Lajos | 128/786 |
| 4,136,703 | 1/1979 | Wittkampf | 128/419 P |
| 4,154,247 | 5/1979 | O'Neill | 128/419 P |
| 4,289,144 | 9/1981 | Gilman | 128/785 |

FOREIGN PATENT DOCUMENTS 9732  4/1980  European Pat. Off. ............. 128/786

*Primary Examiner*—Lee S. Cohen
*Attorney, Agent, or Firm*—Scully, Scott, Murphy and Presser

[57] ABSTRACT

An improved unipolar or bipolar lead for at least S-A Node Atrium Contact to provide atrial pacing or atrial synchronized pacing wherein the distal end of the lead is configured as a S-A Node helix whose coiled diameter is larger than that of the cava.

5 Claims, 9 Drawing Figures

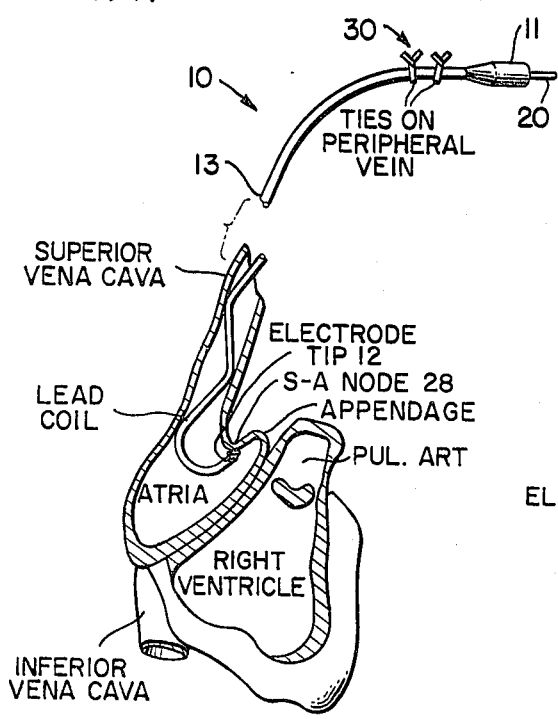
FIG. 1.
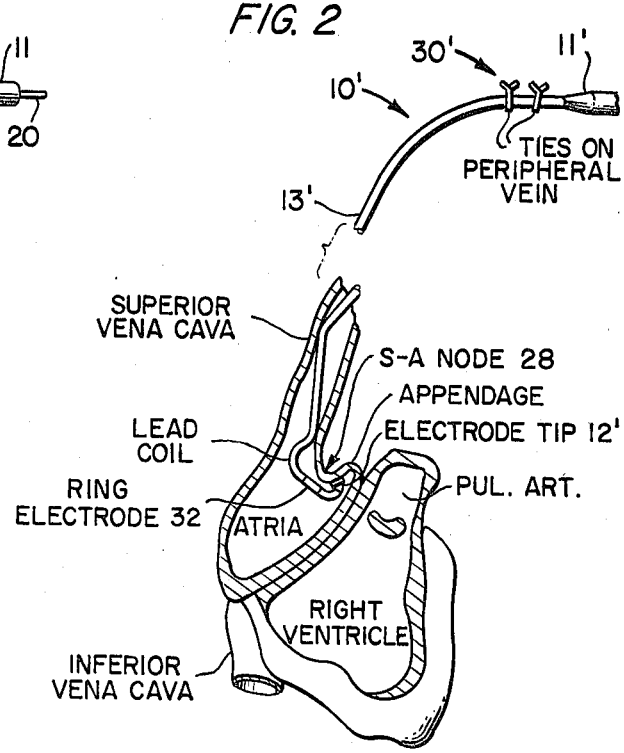
FIG. 2.
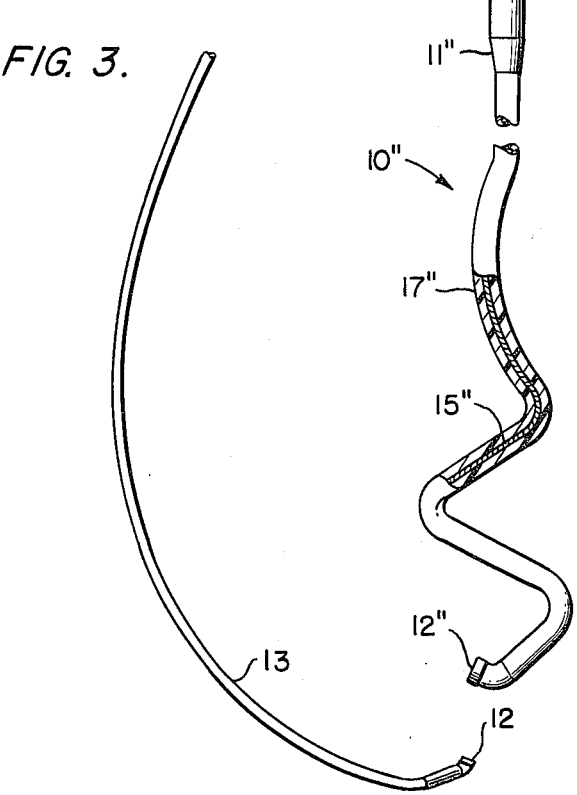
FIG. 3.
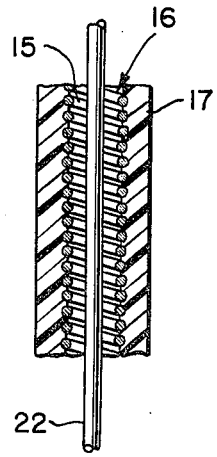
FIG. 9.
FIG. 4.

S-A NODE HELICAL LEAD FOR ATRIAL PACEMAKERS AND METHOD OF PLACEMENT

DESCRIPTION

TECHNICAL FIELD

This invention relates to an improved electrode for Sino-atrial (S-A) node contact in the atrium to provide atrial pacing or atrial synchronized pacing to preserve the contribution of the atrial contraction in the overall cardiac output and at the same time to provide an electrical lead which permits minimization of surgical risk.

BACKGROUND OF THE PRIOR ART

There are approximately 100,000 pacemakers implanted annually, about 10% are of atrial type. One of the major limitations of this type of pacer is the lack of suitable lead. Even so, atrial and atrio-ventricular pacers are being increasingly recommended, and used.

Ventricular stimulating pacemakers are the preferred method of treatment for atrio-ventricular conduction defects, however, 20% of these pacemakers are implanted in patients with sino-atrial nodal disease. The reason that the ventricular pacemakers are used rather than atrial stimulating pacemakers is mainly related to the difficulty in implanting and lack of stability of atrial leads and the resultant poor reliability of P-wave sensing and atrial pacing. By using ventricular stimulating pacemakers, the patient with a normal atrio-ventricular conduction system is deprived of the hemodynamic advantages of atrial systole. This impared function reduces the patient's exercise tolerance and may result in congestive failure in those patients with poor ventricular function.

The advantages of atrial pacemaking are real for both tachycardia and bradycardia syndromes. At present, several basic types of atrial pacemakers are available. One type can be used to pace and sense in atria only. This is merely a modified ventricular pacer. Another senses the P-wave in the atria and then, following an appropriate delay may stimulate the ventricule to pace if the A-V conduction is blocked. Still another type pacer has the ability to sense and pace in both the atria and ventricle. The last two types of pacers may be used in patients with complete A-V block while the last type may be used with S-A nodal bradycardia A-V and/or tachycardia syndromes.

Conventional transvenous ventricular lead systems will not remain in place in the atria, therefore, an atrial lead must be either sutured to the atria directly or a special "J" shape atrial lead may be passed transvenously. It is this latter J-shaped lead system either in unipolar or bipolar configurations which are preferred mainly because of its transvenous placement.

Common forms of the J-lead electrode are disclosed in U.S. Pat. No. 3,939,843 Smyth, and U.S. Pat. No. 3,890,977 Wilson.

The disadvantages of the J-lead include a large diameter ($\geq 8$ Fr) French catheter diameter especially at the radius bend required to maintain the curve; the difficulty in placing such a large stiff lead; and a high dislodgement rate as compared to ventricular leads. In addition, the tip of the J-lead can only be positioned in one place and that is in the atrial appendage, thus negating the ability to position the electrode for minimum pacing threshold and maximum P-wave sensing.

Others have resorted to the use of one or more pliant tines which extend from the electrode tip at an acute angle as "anchor" means to maintain the electrode tip in position. Exemplary of this form of electrode is the electrode disclosed in U.S. Pat. No. 3,902,501 Citron et al.

Flexing of implanted electrodes has also been a problem as such an electrode must flex in the order of 30 million times each year. The Chardack U.S. Pat. No. 3,348,548 and the Lajos U.S. Pat. No. 4,057,067 discloses an electrode wherein the electrical conductor is in the form of spring coils coated with electrically insulating and body compatable material which has now become a fairly uniform procedure for constructing the electrode's conductors.

It is also known to form a cardiac pacer lead which is formable, at the time of pacer implantation by heating the pacer lead as disclosed in the O'Neill U.S. Pat. No. 4,154,247.

BRIEF SUMMARY OF THE INVENTION

This invention is directed to a new lead system specifically designed for atrial sensing and pacing.

The wire electrical conductor coil itself is made of standard materials such as Elgiloy, MP 35N, stainless steel or another corrosion-resistant biocompatible material. It may be made in either unipolar or bipolar in configuration. The bipolar configuration may have the conductor wires side-by-side or coaxial.

The conductor or conductors are then coated with a segmented polyurethane such as Biomer or Pelathane or other similarly biocompatible materials. The coating material is preferably bonded or attached to the lead wire either by a dipping or extruding process so that the coating and wire become bonded, so that the coated electrode will have the ability to be heat-set.

The distal (tip) end of the lead for 6-12 inches is wrapped around a circular mold and the mold and electrode are placed in an oven or other heat source to cause the lead coating to set and hold this coiled or "pig-tailed" shape which, hereinafter will be referred to as the S-A node helical shape.

In use, a stylet is inserted down the center of the spring wire coiled conductor as a stiffener and straightener much the same way as one would use a conventional lead. The lead is then passed transvenously into the patient's heart so that the lead's tip electrode is in the atria. The stylet is now removed so that the lead returns to its original coiled configuration. Now gentle traction is placed on the connector end of the lead so that the lead is slightly withdrawn from the heart at the same time the lead is slowly rotated in a clockwise direction. As the lead is withdrawn, the end of the coil closest to the connector begins to be pulled out of the heart into the cava. The distal end of the lead with the electrode or electrodes (if a bipolar configuration is used) remains in the atria because the coil's diameter is larger than that of the cava. The clockwise rotation, about two turns reforms the helical configuration and cause the electrode tip to be urged against the S-A Node in the Atrium. As more of the lead is withdrawn, the lead becomes more stretched becoming corkscrew-like in appearance.

BRIEF DESCRIPTION OF THE DRAWING

The invention will be more particularly described in reference to the accompanying drawing wherein:

FIG. 1 is a digramic view showing a coiled monopolar lead of the invention positioned in the atria and cava with the spring tension on the lead holding the tip of the lead at the S-A Node area;

FIG. 2 is a diagrammatic view showing the coiled bipolar lead of the invention positioned in the atrial and cava with the spring tension on the lead holding the tip of the lead in the zone of the S-A Node;

FIG. 3 is a view of the lead of the invention in a configuration suitable for insertion;

FIG. 4 is an enlarged fragmentary sectional view of the portion of the lead illustrated in FIG. 1 with a straightening stylet within the coiled conductor;

FIG. 9 is a fragmentary view in partial section of a modified form of the invention.

DETAILED DESCRIPTION OF THE INVENTION

Figure 5:
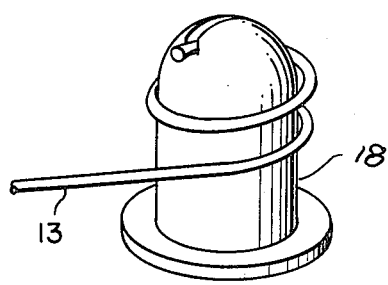
FIG. 5 is a view of a mold for forming the lead of the invention.
Figure 6:
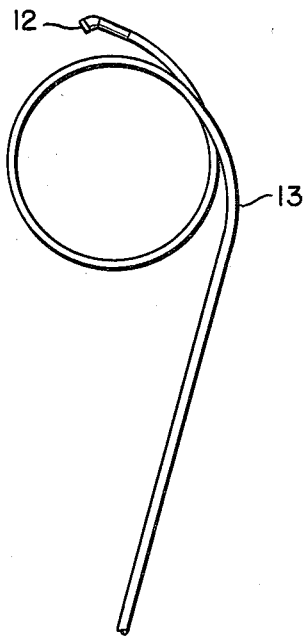
FIG. 6 is a view of the lead illustrated in FIG. 2 in a formed configuration.
Figure 7:
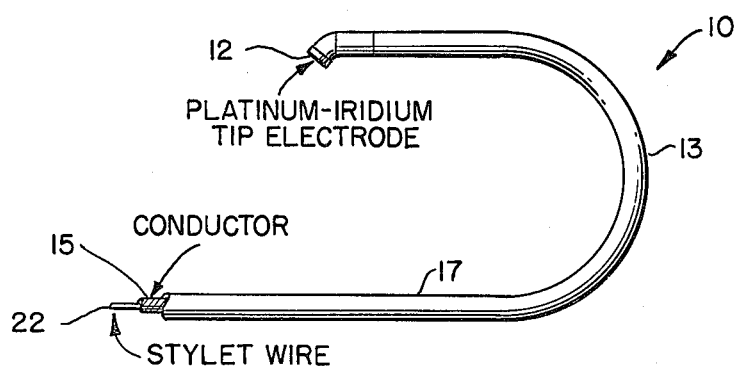
FIG. 7 is a fragmentary view of a portion of a monopolar lead of the invention.

One form of the invention will be specifically described in reference to a unipolar pacer lead as illustrated in FIGS. 1, 3, 4, 5, 6, 7 and 9 of the drawing. The lead, generally designated 10 has a connector portion 11, electrode portion 12 and central portion 13. The cross section of the central portion 13 may be as illustrated in FIG. 4. That is, an electrical conductor formed of a coiled member 15 having a void lumen 16 encased in an insulating material 17 which is generally inert in body fluids and tissue.

The wire electrical conductor coil 15 may be formed of standard material such as ELGILOY, MP-35N, stainless steel, DBS or other corrosion resistance biocompatable material.

The conductor coil 15 diameter may be the standard 0.040 inch or preferably have a larger helical coil diameter such as 0.065 for added flexural strength. The coil 15 is preferably coated with a segmented polyurethane 17 such as Biomer or Pelathane or other similarly biocompatible materials. The coating material is preferably bonded or attached to the lead wire either by a dipping or extruding process so that the coating and wire become bonded. A coating to provide overall outside diameter in the order of (<6 Fr) is maintained and yet the lead will have improved strength and have the ability to be heatset. The distal tip end of the lead 10 for 6–12 inches is wrapped around a circular mold 18 with a diameter of between one and three inches. This mold's diameter, and thus the lead's resultant coil diameter should be approximately one and one-half to two times the diameter of the superior vena cava into which the lead is to be inserted. The lead end should encircle the mold so that between one and three complete revolutions are made, either clockwise or counter-clockwise, as detailed hereinafter. The lead is then placed in an oven or other heat source to cause the lead coating to set and hold this coiled or "pig-tailed" shape. For the segmented polyurethane material (Biomer or Pelethane) a temperature range of 260°–275° F. for 45 minutes is adequate.

In construction of the lead, selecting a lead having a coil diameter in the range of about 0.020 to about 0.100 and preferably about 0.060 for the conductor coated with a segmented polyurethane to an outside diameter in the order of 4–8 Fr heat set for about 30–120 minutes at a temperature range of 250–350 and preferably about 260° F. the resulting coil is slinky or weak that it does not matter which way the lead is wound onto the mold 18 that is whether the lead is wound clockwise or counterwise. The subequent twisting, axially of the lead clockwise, after placement in the atrium cause the lead to form a clockwise helix. However, with a larger diameter conductor coil, or a heavier or thicker coating of segmented polyurethane, or a higher setting temperature or a longer setting time or a combination of more than one of these factors, which results in a stiffer lead, it would be necessary to wind the lead on the mold in a clockwise direction for heat setting. Further, it will be appreciated that the heat set coil can not properly function unless the normal body movements are sufficient to cause the helical coil to expand and contract, otherwise body movement may cause the electrode tip of the lead to move from its S-A Node sensing position.

Alternate to heat-setting the urethane coating, conductive wire with a special memory helical coil that would cause the lead to retain the S-A nodal coiled shape and yet be able to stretch could be used.

In the lead of the invention the distal portion of the lead is coiled for at least 1½ to 2½ complete or more turns in the unretracted state. This is necessary to maintain the stretched helical coil configuration when traction is used to position the electrode at the S-A Node area.

In general the diameter of the distal helical coil or twist in the lead is based upon the cava diameter. It must be a diameter larger than the cava (probably 1½ to 2 times). This then allows the lead to extend out into slinky or soft spring coil in the cava when traction is applied to the connector end thereof and acts as a shock absorber spring when the body or heart move. The lead then is held in place by the action of tip extending into and hooking around into the atria at the cava-atria junction and the coil trying to return to this original configuration.

Although a coil diameter of approximately 0.060 inch would seem optimum, smaller (0.020) and larger coils (0.10) may also be adaptable depending on the method and materials used in construction. In addition, in the bipolar version, which may be preferred mode, the coils could be coaxial (0.20 inside an 0.060) or side-by-side (two 0.040 inch coils).

The conductor 15 is in electrical contact with a conductive tip 12 and extends from the conductive tip 12 through the central portion 13 and the connecting portion 11 and into electrical contact with a connecting pin 20. the connecting pin 20 is adapted for connection with a remote electrical device in known manner and has a lumen therethrough coincident with the lumen 16 of the conductor 15. With this configuration, it is possible to insert a stylet 22 through the end of the connecting pin 20, through the lumen 16 of conductor 15 into abutment with the conducting tip 12. The electrically conductive tip 12 may be of any material suitable for the environment, platinum-iridium, for example.

In use, a stylet 22, of conventional form, is inserted down the center as stiffener and straightener much the same way as one would use a conventional lead.

The lead is then passed transvenously into the patient's heart so the lead's tip electrode is in the atria (FIG. 1). The stylet is then removed so that the lead is urged to return to its original coiled configuration in the atria.

Now gentle traction is placed on the connector end of the lead so that the lead is being withdrawn from the heart. As the lead is withdrawn, the end of the coil closest to the connector begins to be pulled out of the heart into the cava. The distal coil end of the lead with the electrode tip or electrodes (if a bipolar configuration is used) remains in the atria longest because the lead's helical coil diameter is larger than that of the cava. As more of the lead is withdrawn, several clockwise axial turns of the lead are made via the connector hub 11, causing the lead to be stretched and corkscrewlike or helical in appearance similar to that of a stretched spring (FIG. 1).

These clockwise turns are transmitted down the lead causing the lead to assume its helical coiled configuration and causing the electrode tip 12 to rotate into contact that the S-A Node area 28. The clockwise axial turns imparted to the lead are made regardless of whether the lead was wound and heat set in the clockwise or counterclockwise direction.

While the lead is being withdrawn the leads position is monitored fluoroscopically. The P-wave amplitude also maybe observed electrocardiographically by monitoring between the tip and subcutaneous ground (unipolar lead) or between the tip and the ring (bipolar configuration). The lead may be withdrawn until the tip is placed in the cava-atria junction (FIG. 1). It is this position that is the anatomic location of the S-A Node and where maximum P-wave amplitude may be detected.

Once positioned, the lead is ligated at 30 (FIG. 1), in place at the pacemaker implant site and connected to a pacemaker. Stability of the lead is maintained because the spring tension of the lead in the cava allows the lead to move freely in and out as the lead tries to return to its present coil diameter. The cava will hold the lead stably in this elongated spring or corkscrew shape and the tip will continue to be gently but firmly lodged at the S-A Nodal area 28 (FIG. 1 and 2).

Figure 8:
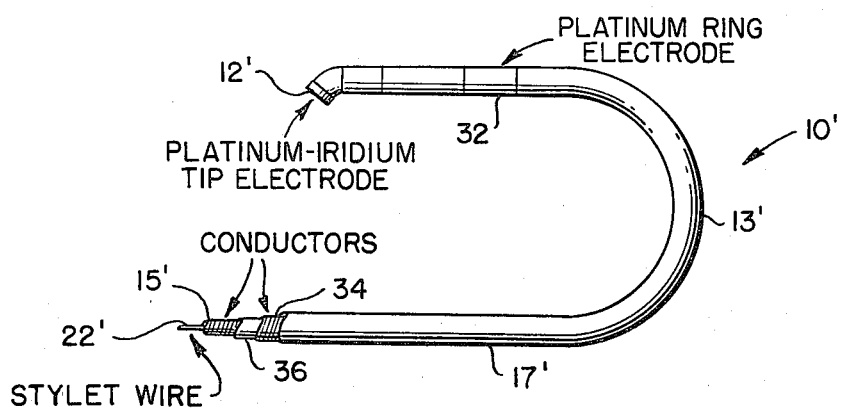
FIG. 8 is a view like FIG. 7 of a bipolar lead.

Referring now to FIGS. 2 and 8 there is illustrated a bipolar form of the lead of the present invention.

In FIGS. 2 and 8 10' generally designates the bipolar lead having a connector portion 11', an electrode portion 12', a space ring conductor 32 and a central portion 13'. The electrode tip 12' of the lead 10' is connected to the connector 11' via a wire electrical conductor coil 15' whereas the ring electrode 32 is electrically connected to the connector 11' via the wire electrical conductor coil 34.

The two conductor coils 15' and 34 are separated electrically by an insulating layer 36 which may comprise segmented polyurethane as is the outer insulating material 17 as discussed in reference to the unipolar pacer lead hereinbefore described.

the inner conductor 15' is provided with a void lumen such as lumen 16 of the unipolar lead. The lumen is sized to receive the stylet designated 22' which stylet is employed to straighten and stiffen the electrode during insertion of the patient's atrium. In an example of a bipolar lead the ring electrode 32 area would be in the order of 25 to 75 square millimeters and would be spaced from, for example, 1.5 to 3 centimeters from the tip electrode 12'.

Referring now specifically to FIG. 2, it will be noted that the electrode tip 12' is positioned substantially at the S-A Node which then positions the ring electrode 32 a few centimeters toward the superior vena cava from the S-A Node. it is not necessary that the ring electrode 32 be in actual contact with any portion of the atria as the blood in the atria acts as an electrical conductor thereby transmitting electrical signals from the atria to the ring electrode.

As in the case of the unipolar electrode approximately 6-12 inches of the distal end thereof is for example wrapped about a cylindrical mold and maintained in such wrapped conditions until the segmented polyurethane exterior insulative coating 17' and/or the internal insulator 36 are heat set to provide the lead with a coiled or "pig-tailed" configuration.

As described in reference to the unipolar lead, the lead 10' is coiled for at least one-and-a-half to two-and-a-half or more complete turns in the unretracted state.

Insertion and placement of the bipolar lead is the same as that employed in placement of unipolar lead and will not be repeated herein.

Referring to FIG. 9 there is shown a modified form of the present invention, wherein the helical coil configuration is imparted by the electrical conductor rather than by the heat set biocompatible coating as described in reference to the other forms of the invention.

In FIG. 9, 10'' generally designates a single conductor lead comprising a metallic conductor coil 15'', and insulating biocompatible coating 17'' which may consist of urethane, silicone rubber or the like. At the distal end of the conductor coil 15'' is an electrode tip 12'' and at the opposite end is a connector portion 11'' having a male connector pin 20''.

The wire coil conductor 15'' is constructed of heavier gauge wire than the conductors 15 and 15', which conductor coil is heat treated or tempered to maintain the helical configuration. It is only necessary that the heavier gage wire comprise the distal end portion of the lead for, 6 to 12 inches.

Where this form of the invention is employed in a two conductor configuration for bipolar sensing only the outer most wire conductor of a coaxial configuration would be required to have the helical memory imparted thereto.

The advantages of the leads of the invention lie in their ease of placement, their long term stability and the position of the tip in a more electrically active area of the atria. Placement is simply a matter of inserting a stylet-straightened lead, removing the straightening wire, turning the lead clockwise axially about two turns, then withdrawing the lead several inches to stretch the coil out in the cava. The tip remains stable against the atria wall at the S-A nodal area. By having this coiled configuration, the lead can move around in the cava, yet it will remain sprung out against the walls. This lead relies on the heart's own anatomy and the helical coil itself acts as a shock absorber trying to return a present diameter. Thus the lead is passively fixed and less irritating to the heart and conductive tip of the lead is placed at the S-A Nodal area.

I claim:

1. An improved electrically conductive lead for at least S-A Node Atrium Contact to provide atrium pacing and sensing comprising an electrical conductor having a lumen there through, an electrode tip, said electrode tip being electrically connected to the electrical conductor adjacent one end of the conductor, and S-A Node helix, said helix extending from the electrode tip toward the other end of the electrical conductor a distance of 6 to 12 inches and having at least one-and-a-half turns and a non-conductive biocompatable coating encasing the electrical conductor except the electrode tip.

2. The invention defined in the claim 1 wherein the diameter of the helix is between 1 and 3 inches.

3. The lead as defined in claim 1 wherein the conductor coating comprises segmented polyurethane and the S-A Node helix configuration is heat set.

4. An improved electrically conductive lead for at least S-A Node Atrium Contact to provide atrium pacing and sensing comprising an electrical conductor having a lumen there through, an electrode tip, said electrode tip being electrically connected to the electrical conductor adjacent one end of the conductor, an S-A Node helix, said helix extending from the electrode tip toward the other end of the electrical conductor a distance of 6 to 12 inches, and a non-conductive biocompatible coating encasing the electrical conductor except the electrode tip wherein the helix configuration is made by using a conductive wire with a memory helical coil that would cause the lead to maintain its helical shape and yet be able to be stretched.

5. A method for at least S-A Node Atrial pacing and sensing comprising the steps forming an electrically conductive lead having a hollow lumen axially therein from an electrical conductor having a tip electrode electrically connected to the conductor, forming the end of the conductor having the electrode tip into a helix having at least one-and-a-half turns, inserting a stylet in the lumen of the lead to cause the lead including its electrode tip end to be straightened, inserting the stylet straightened lead in the atria of a patient via the superior vena cava; removing the stylet from the lumen of the lead to allow the lead to return to its original helix configuration in the atria; slightly retracting the lead and imparting several clockwise axial turns to the lead to cause contact between the atrium at the S-A Node, with the tip electrode of the conductor.

* * * * *